(12) United States Patent
Kumar et al.

(10) Patent No.: US 7,066,736 B2
(45) Date of Patent: Jun. 27, 2006

(54) DENTAL IMPRESSION COPING WITH RETENTION

(75) Inventors: Ajay Kumar, Palmdale, CA (US); Ines Aravena, Camarillo, CA (US)

(73) Assignee: Zimmer Dental, Inc., Warsaw, IN (US)

( * ) Notice: Subject to any disclaimer, the term of this patent is extended or adjusted under 35 U.S.C. 154(b) by 168 days.

(21) Appl. No.: 10/302,128

(22) Filed: Nov. 22, 2002

(65) Prior Publication Data

US 2004/0101806 A1   May 27, 2004

Related U.S. Application Data

(60) Provisional application No. 60/410,073, filed on Sep. 12, 2002.

(51) Int. Cl.
*A61C 8/00* (2006.01)

(52) U.S. Cl. ...................................... 433/173; 433/172

(58) Field of Classification Search ................ 433/172, 433/173, 174, 175, 176
See application file for complete search history.

(56) References Cited

U.S. PATENT DOCUMENTS

| | | | |
|---|---|---|---|
| 3,708,883 A | 1/1973 | Flander | |
| 3,878,610 A | 4/1975 | Coscina | |
| 4,011,602 A | 3/1977 | Rybicki et al. | |
| 4,708,654 A | 11/1987 | Brånemark | |
| 4,744,753 A | 5/1988 | Ross | |
| 4,778,386 A | 10/1988 | Spiry | |
| 4,850,870 A | 7/1989 | Lazzara et al. | |
| 4,854,872 A | 8/1989 | Detsch | |
| 4,955,811 A | 9/1990 | Lazzara et al. | ............. 433/173 |
| 4,961,706 A | 10/1990 | Jefferies | |
| 5,004,421 A | 4/1991 | Lazarof | |
| 5,022,860 A | 6/1991 | Lazzara et al. | |
| 5,074,791 A | 12/1991 | Shoher et al. | |
| 5,078,606 A | 1/1992 | Söderberg | |
| 5,087,199 A | 2/1992 | Lazarof | |
| 5,094,620 A | 3/1992 | Nordin | |
| 5,106,299 A * | 4/1992 | Ghalili | ...................... 433/172 |
| 5,106,300 A | 4/1992 | Voitik | |
| 5,120,223 A | 6/1992 | Weissman | |
| 5,125,839 A | 6/1992 | Ingberg et al. | |
| 5,125,841 A | 6/1992 | Carlsson et al. | |
| 5,135,395 A | 8/1992 | Marlin | |
| 5,192,207 A | 3/1993 | Rosellini | |
| 5,195,891 A | 3/1993 | Sulc | |
| 5,302,125 A | 4/1994 | Kownacki et al. | |
| 5,332,390 A | 7/1994 | Rosellini | |
| 5,344,457 A | 9/1994 | Pilliar et al. | |
| 5,350,302 A | 9/1994 | Marlin | |
| 5,385,469 A | 1/1995 | Weissman | |
| 5,417,570 A | 5/1995 | Zuest et al. | |
| 5,470,230 A | 11/1995 | Daftary et al. | |

(Continued)

FOREIGN PATENT DOCUMENTS

DE    31 10 694    9/1982

(Continued)

*Primary Examiner*—John J Wilson
(74) *Attorney, Agent, or Firm*—Conley Rose, P.C.

(57) ABSTRACT

An impression coping for taking an impression of a dental implant installed in the jawbone of a patient. The impression coping has a proximal end with an impression portion adapted to be embedded in impression material and a distal portion with a retention mechanism. The retention mechanism includes a housing having a locking member and biasing member. The locking member is biased to slideably move in the housing and engage the dental implant.

7 Claims, 3 Drawing Sheets

U.S. PATENT DOCUMENTS

| | | | |
|---|---|---|---|
| 5,487,663 A | 1/1996 | Wilson |
| 5,489,210 A | 2/1996 | Hanosh |
| 5,513,989 A | 5/1996 | Crisio |
| 5,527,182 A | 6/1996 | Willoughby |
| 5,538,426 A | 7/1996 | Harding et al. |
| 5,556,278 A | 9/1996 | Meitner |
| 5,564,921 A | 10/1996 | Marlin |
| 5,564,924 A | 10/1996 | Kwan |
| 5,571,016 A | 11/1996 | Ingber et al. |
| 5,624,263 A | 4/1997 | Babaian |
| 5,658,147 A | 8/1997 | Phimmasone |
| 5,662,476 A | 9/1997 | Ingber et al. |
| 5,681,167 A | 10/1997 | Lazarof |
| 5,685,715 A | 11/1997 | Beaty et al. |
| 5,688,123 A | 11/1997 | Meiers et al. |
| 5,722,832 A | 3/1998 | White |
| 5,725,375 A | 3/1998 | Rogers |
| 5,762,500 A | 6/1998 | Lazarof |
| 5,829,977 A | 11/1998 | Rogers et al. |
| 5,871,358 A | 2/1999 | Ingber et al. |
| 5,873,721 A | 2/1999 | Willoughby |
| 5,882,200 A | 3/1999 | Sutter et al. |
| 5,890,896 A | 4/1999 | Padial |
| 5,899,695 A | 5/1999 | Lazzara et al. |
| 5,904,483 A * | 5/1999 | Wade ................. 433/173 |
| 5,947,736 A | 9/1999 | Behrend |
| 5,993,211 A | 11/1999 | Broberg |
| 6,030,219 A | 2/2000 | Zuest et al. |
| 6,056,547 A | 5/2000 | Names |
| 6,068,478 A | 5/2000 | Grande et al. |
| 6,142,782 A | 11/2000 | Lazarof |
| 6,159,010 A | 12/2000 | Rogers et al. |
| 6,213,773 B1 | 4/2001 | Gittleman |
| 6,217,331 B1 | 4/2001 | Rogers et al. |
| 6,227,856 B1 | 5/2001 | Beaty et al. |
| 6,283,752 B1 | 9/2001 | Kumar |
| 6,299,447 B1 | 10/2001 | Zuest |
| 6,332,777 B1 * | 12/2001 | Sutter ................. 433/173 |
| 6,394,809 B1 | 5/2002 | Rogers et al. |
| 6,488,501 B1 | 12/2002 | Harding |
| 6,508,650 B1 | 1/2003 | Gittleman |
| 6,540,514 B1 | 4/2003 | Falk et al. |
| 6,672,871 B1 | 1/2004 | Hurson |
| 6,758,672 B1 | 7/2004 | Porter et al. |
| 6,758,782 B1 | 7/2004 | Mattzschker et al. |
| 6,824,386 B1 | 11/2004 | Halldin et al. |
| 2001/0034008 A1 | 10/2001 | Porter et al. |
| 2002/0039718 A1 | 4/2002 | Kwan |
| 2002/0106610 A1 | 8/2002 | Hurson |
| 2003/0082499 A1 | 5/2003 | Halldin et al. |
| 2003/0175655 A1 | 9/2003 | Klardie et al. |
| 2003/0190586 A1 | 10/2003 | Falk et al. |
| 2003/0211445 A1 | 11/2003 | Klardie et al. |
| 2004/0096804 A1 | 5/2004 | Vogt et al. |
| 2004/0209226 A1 | 10/2004 | Rogers et al. |
| 2004/0209227 A1 | 10/2004 | Porter et al. |
| 2004/0241610 A1 | 12/2004 | Hurson |

FOREIGN PATENT DOCUMENTS

| | | |
|---|---|---|
| DE | 33 00 764 | 7/1984 |
| DE | 43 26 841 | 2/1995 |
| DE | 298 20 971 | 11/1998 |
| EP | 0 087 578 | 2/1982 |
| EP | 0 879 024 | 2/1996 |
| EP | 0 879 025 | 2/1996 |
| EP | 1 082 065 | 12/1999 |
| EP | 1 118 312 | 7/2001 |
| EP | 0 986 343 | 8/2004 |
| WO | WO96/29019 | 9/1996 |
| WO | WO 97/17907 | 5/1997 |
| WO | WO 97/24996 | 7/1997 |
| WO | WO 97/28756 | 8/1997 |
| WO | WO 99/62421 | 12/1999 |
| WO | WO00/02497 | 1/2000 |
| WO | WO224104 A1 * | 3/2002 |
| WO | WO 03/030768 | 4/2003 |
| WO | WO 03/037207 | 5/2003 |

* cited by examiner

DENTAL IMPRESSION COPING WITH RETENTION

CROSS-REFERENCE TO RELATED APPLICATIONS

This application claims benefit of priority of U.S. Provisional Application Ser. No. 60/410,073 filed Sep. 12, 2002.

FIELD OF THE INVENTION

The present disclosure relates to dental impression copings for taking impressions of a dental implant site from which accurate models can be constructed. More particularly, the invention relates to an improved impression coping that utilizes a retention mechanism to connect with the dental implant.

BACKGROUND OF THE INVENTION

Implant dentistry involves the restoration of an edentulous area in the mouth of a patient. The restorative techniques typically use artificial components, such as abutments and prosthetic teeth that are secured to a dental implant. According to state of the art techniques, this restorative process has several stages.

During an initial stage, the jawbone of the patient is exposed, and a series of drills are used to form a cylindrical cavity (the osteotomy) in the bone. A dental implant is then positioned into the cavity. In a two-stage surgical procedure, the gingival tissue is sutured, and the implant is left in the bone for several months to integrate with surrounding bone and tissue. In a single-stage procedure, this bone-integration period is skipped.

During the next stage, a mold or impression is taken to record the position and orientation of the implant within the mouth. The impression is used to create a plaster model or analogue of the implantation site. This model replicates the placement of the implant and enables dental technicians to fabricate a final prosthetic restoration. After the impression is taken, a temporary healing abutment or temporary prosthesis is attached to the implant. At this time, the gingival tissue is contoured or shaped to receive the final restoration.

In order to produce a final restoration with excellent aesthetics and functionality, the analogue must accurately reflect the position and orientation of the implant in the mouth of the patient. To help achieve this accuracy, one or more indexing means are typically provided on the proximal end of the implant and on the distal end of the impression coping. Typically, the indexing means is a hexagonal projection or indentation or other polygon formed at the coronal end of the implant. When the implant is fully installed in the jawbone of the patient, the indexing means is typically exposed through the crestal bone so that accurate mapping of the implant and surrounding jawbone can occur. However, because the indexing means of the implant is typically quite small and may be recessed partially beneath the gums of a patient, a secondary or intermediate impression element is typically used to help accurately transfer the orientation of the indexing means of the implant. This intermediate impression element is commonly called a "coping" or "impression coping." Examples of impression copings are taught in U.S. Pat. No. 4,955,811 entitled "Non-rotational Single-Tooth Prosthodontic Restoration" to Lazzara et al.

Today, two types of impression copings are used: Transfer impression copings that use an "open-tray" technique, and pick-up impression copings that use a "closed-tray" technique. Both types are conveniently adapted to be screw-retained to the implant. The choice of which technique to use (open tray vs. closed tray) is primarily based on individual patient characteristics and preferences of the clinician.

In the closed-tray technique, a threaded screw or bolt is used to temporarily secure the impression coping to the implant fixture. Once the coping is secure, a U-shaped impression tray filled with impression material is placed in the patient's mouth over the implant site. The patient bites down on the tray and squeezes the impression material into the implantation site and area around the impression coping. Within a few minutes, the impression material cures or hardens to a flexible, resilient consistency. The impression tray is then removed from the patient's mouth to reveal an impression of the implant site and coping. The screw connecting the implant is unthreaded, and the impression coping is removed. The coping is then removed from the mouth of the patient and is transferred back into the impression material.

One advantage of the closed-tray technique is that it is simple to perform. The technique, however, is sometimes prone to inaccuracies where sufficient care is not taken during the step of reinserting the coping into the impression material.

The open-tray technique is similar to the closed-tray technique except that a pick-up coping, instead of the transfer coping, is used. The pick-up coping typically includes a portion adapted to be embedded in the impression material. This portion includes a protuberant "lip" or similar projection at the coronal aspect so the coping can be retained in the impression material. In this case, once the impression is taken and the tray is removed, the coping remains in the impression material or is "picked up" and pulled away from the mouth of the patient. To facilitate this procedure, the tray is provided with one or more apertures or openings through which a tool may be inserted to loosen the screw or bolt securing each coping. Thus, this impression technique is commonly referred to as the "open-tray" technique.

The open-tray technique is particularly well suited for multi-site dental restoration procedures, especially when a large divergence angle exists between multiple adjacent implants. The open-tray technique is generally preferred for accuracy, but it is more complex since holes or apertures may need to be cut in the tray. As a result, this technique often takes more time to prepare and execute.

It would be advantageous to have an impression coping that has advantages over prior impression copings and techniques.

BRIEF SUMMARY OF PREFERRED EMBODIMENTS OF THE INVENTION

The present invention is directed toward an impression coping for taking an accurate impression of a dental implant installed in the jawbone of a patient. The impression coping has a body that extends from a proximal portion to a distal portion. The distal portion is configured and adapted to be secured to the implant, and the proximal portion includes an attachment portion adapted to be embedded in an impression material. Preferably, two attachment members form part of the attachment portion and comprise separate, spaced polygons that project outwardly from the body.

A retention mechanism is located on the body at the distal portion. The retention mechanism is sized and shaped to engage the coronal end of the implant and includes a housing having a locking member and a biasing member. Preferably, the housing forms a bore perpendicular to a longitudinal axis that runs through the body. At one end of the bore, the biasing member is positioned to bias the locking member. The locking member slideably moves along the bore and partially protrudes from the housing to engage a surface at the coronal end of the dental implant. In one embodiment, the locking member is a ball, pin, cylinder, or the like; and the biasing member is a spring.

The housing can be a separate unit and attachable to the distal portion of the body of the impression coping. As such, the retention mechanism and body are easily manufactured and connected. Further, different designs can be employed with the retention mechanism. This mechanism, for example, can utilize multiple locking members and biasing members housed together at the distal portion of the body.

The coping also includes an indexing component, such as a boss or recess, formed for interlockingly engaging a corresponding mating indexing component formed at the coronal end of the implant. Further, the coping may be used as either a transfer coping or pick-up coping, as desired.

As one important advantage of the present invention, connection between the coping and implant does not require a separate retaining screw. Rather, the connection occurs with active or moveable biasing and locking members. Since a retaining screw is not needed, several steps can be eliminated while performing an open-tray impression technique. These steps include: threading the screw into the implant; opening or drilling holes in the impression tray; and unthreading the screw prior to removing the coping from the implantation site. The elimination of these steps saves valuable time during the dental surgery and reduces costs.

As another advantage, the connection between the coping and implant will not damage the internal cavity of the implant and offers a reliable, consistent engagement with the implant.

As another advantage, the retention mechanism is well suited for multi-teeth restorations, especially when some of the implants are angled with respect to one another. In this situation, when the implants are not all vertically oriented, the copings are less prone to jam or wedge when the impression tray is lifted and removed from the mouth of the patient.

As yet another advantage, the retention mechanism is durable and formed of a corrosive resistant and biocompatible material well suited for implant dentistry. This mechanism is easily manufactured and connected to the distal portion of the body.

Accordingly, the present invention comprises a combination of features and advantages that overcome various problems, deficiencies, or shortcomings associated with prior devices. The various features and advantages of the invention will be readily apparent to those skilled in the art upon referring to the accompanying drawings and reading the following detailed description of the preferred embodiments of the invention.

BRIEF DESCRIPTION OF THE DRAWINGS

For a more detailed description of preferred embodiments of the present invention, reference will now be made to the accompanying drawings, wherein.

DETAILED DESCRIPTION OF PREFERRED EMBODIMENTS

Figure 1:
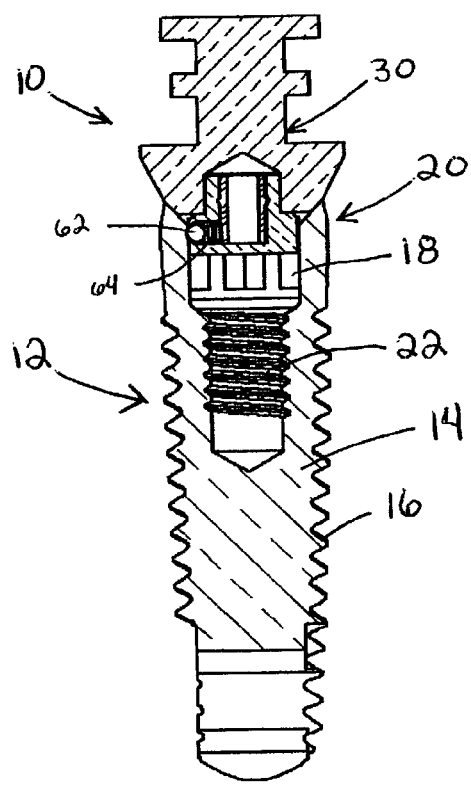
FIG. 1 illustrates a cross-sectional view of an impression coping of the present invention connected to a dental implant.

FIG. 1 illustrates a dental impression coping 10 of the present invention connected to a dental implant 12 suited for receiving the coping. The implant 12 can be any one of a wide variety of dental implants, for example, a threaded implant, a cylindrical implant, or a tapered implant, as are known in the art. Such an implant could be a tapered or straight Screw-Vent implant of Centerpulse Dental Inc.

As shown in FIG. 1, the implant comprises a body or root portion 14 adapted to engage an osteotomy or alveolar cavity in the jawbone of a patient. The body includes external threads 16 adapted to engage bone in the osteotomy. The implant also includes a hexagonal recess or bore 18 at a top or coronal end 20. This recess includes an internally threaded portion or socket 22 that extends into the body portion of the implant. The threaded socket 22 is adapted to threadably engage a retaining screw (not shown).

The hexagonal recess 18 of the implant is configured to provide anti-rotational engagement with various dental components, such as the impression coping of the present invention. Alternatively, this anti-rotational engagement could be provided as a hexagonal post or protrusion to engage a corresponding recess. Further, as known to those skilled in the art, other anti-rotational connections (such as octagons, triangles, stars, splines, and the like) are also available.

Figure 2:
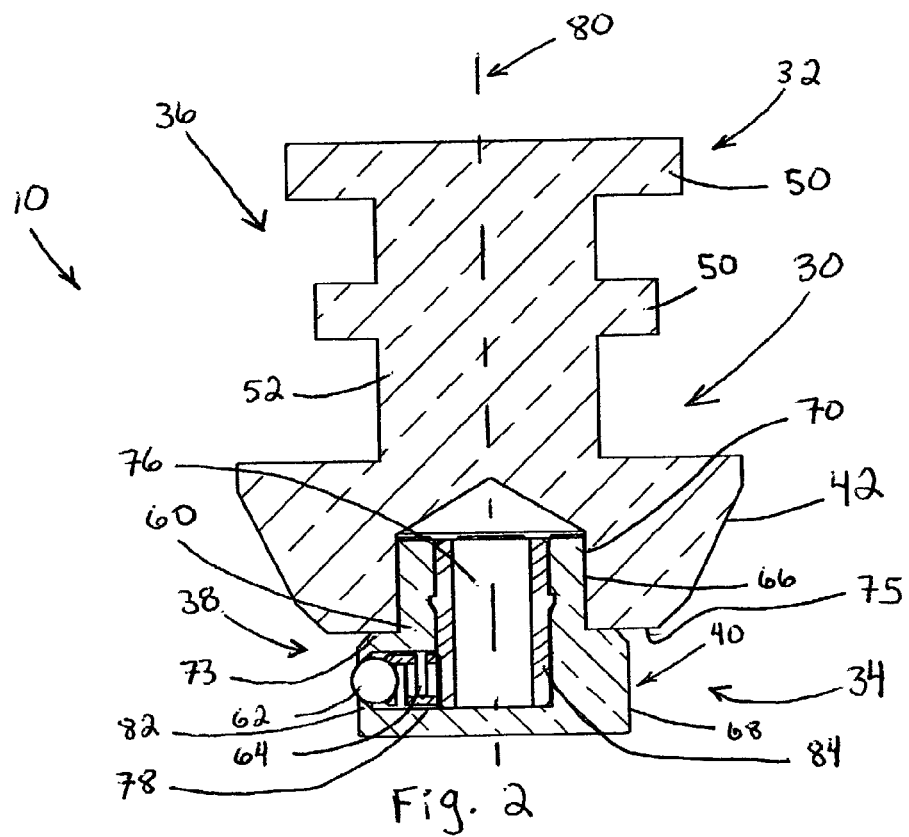
FIG. 2 illustrates an enlarged cross-sectional view of the impression coping of FIG. 1.
Figure 3:
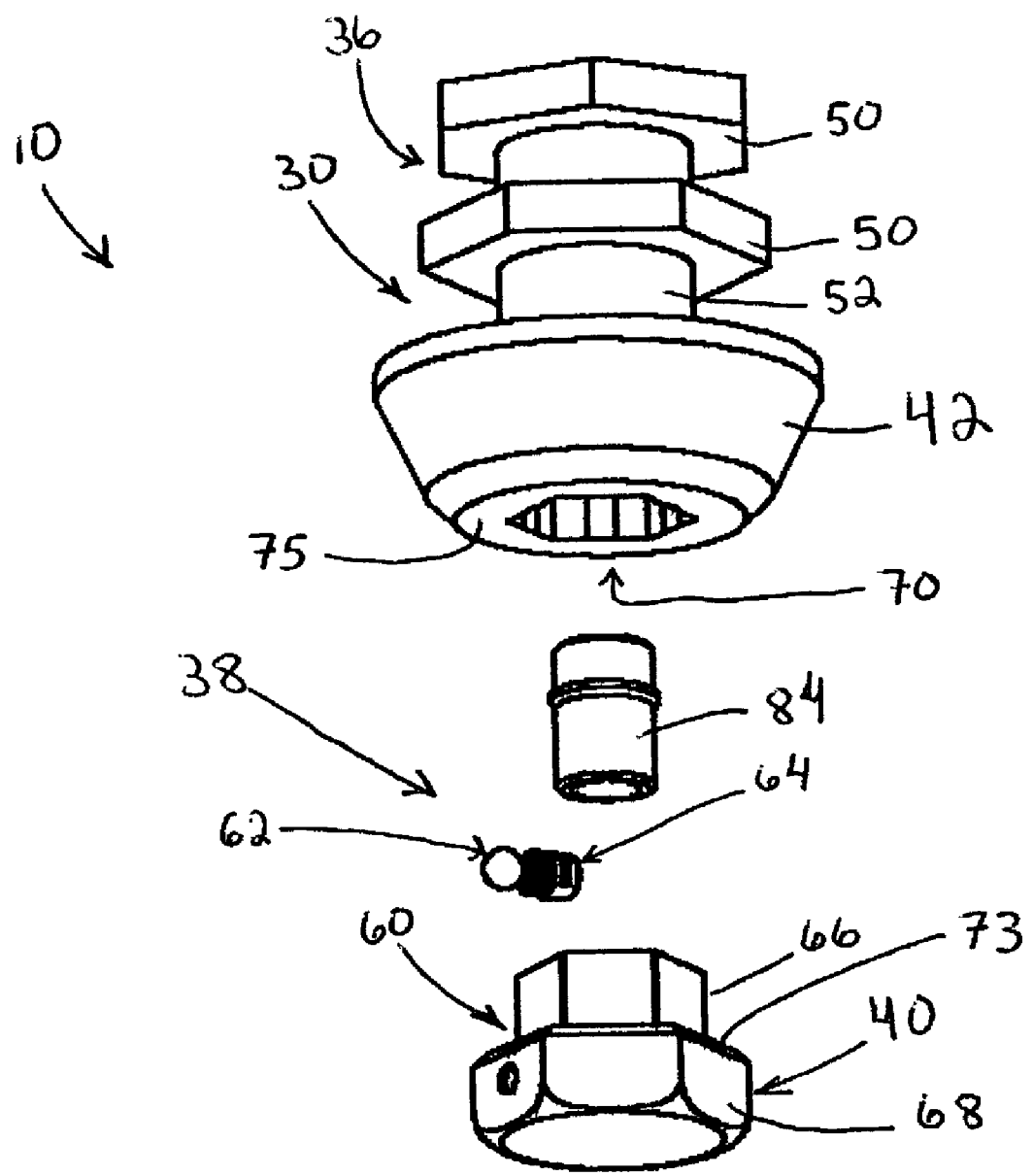
FIG. 3 illustrates an exploded view of the impression coping of FIG. 1.

FIGS. 1–3 illustrate one embodiment of the impression coping 10 having features and advantages in accordance with the present invention. The coping comprises a body 30 that extends from a proximal portion 32 to a distal portion 34. The proximal portion includes an attachment portion or impression area 36, and the distal portion includes a retention mechanism 38 and an indexing or engagement portion 40. A cover 42 extends between the attachment portion and retention mechanism. The cover has a rounded dome or frusto-conical shape.

The attachment portion 36 is adapted to be embedded in impression material. This portion includes two attachment members 50 that extend outwardly from a cylindrical portion 52 of body 30. Each attachment member is formed as a flat hexagon extending between top and bottom surfaces. The hexagons are parallel with one another, with one hexagon being larger than the other.

Although the attachment portion 36 is shown to have two attachment members 50, it will be appreciated that other configurations adapted to be embedded in impression material will work as well. The attachment portion, for example, could include one or more attachment members formed as polygons other than hexagons. Regardless of the geometry, the attachment members preferably are ergonomic and sized to be fit in all areas of the jawbone, including the lower anterior mandible where interproximal space between adjacent dentition or abutments is minimal.

As noted, distal portion 34 of body 30 includes an indexing portion 40. This portion is configured as a hexagonal protrusion and is adapted to engage the hexagonal recess or bore 18 at the coronal end 20 of the dental implant. Together, bore 18 and the hexagonal protrusion 40 connect to provide anti-rotational engagement between the impression coping and dental implant.

Like the hexagonal recess 18 of the implant 12, the indexing portion 40 may be formed in a wide variety of other shapes that may be used to provide anti-rotational connection between the implant and impression coping. For example, the indexing portion could comprise either a recess or protrusion formed as various polygons and other configurations known to those skilled in the art, such as an octagon, triangle, square, star, spline, etc.

As best shown in FIGS. 2 and 3, the retention mechanism 38 includes a housing 60 and a locking member 62 and a biasing member 64 located in the housing. Preferably, the housing 60 is formed as a top cylindrical engagement portion 66 and a bottom cylindrical engagement portion 68. Both top and bottom portions have external hexagonal surfaces. The bottom portion 68 serves as the indexing portion 40 to mate with the implant, as described above. The top portion is adapted to fit in a hexagonal recess or bore 70 located in the body. Connection between the housing and body occurs when the top portion 66 is press-fit into the bore 70. When fully seated, a top, flat surface 73 of the top portion 66 seats against a bottom, flat surface 75 of cover 42. The press-fit connection can be designed to be permanent or removable, depending on design considerations.

Although the top engagement portion 66 and recess 70 are shown as male and female hexagons, respectively, other configurations known to those skilled in the art can be employed as well. For example, mating recesses and protrusions can be used for either component. Further, the recess and protrusion can be formed as various polygons and other configurations known to those skilled in the art, such as an octagon, square, triangle, star, spline, etc.

As best shown in FIG. 2, housing 60 includes two separate cylindrical bores: A longitudinal bore 76 and an axial bore 78. These bores are perpendicular, with the longitudinal bore being concentric with a longitudinal axis 80 of body 14. Preferably, the axial bore extends from the exterior surface of the bottom portion 68 to interconnect with the longitudinal bore 76.

Preferably, the locking member is formed as a ball, and the biasing member is formed as a spring. Both the ball and spring are located in the axial bore 78 to slideably move in the bore. Specifically, one end of the spring is abutted against the ball to bias the ball partially out of the bore 78. A lip or ridge 82 is located at one end of the bore to prevent the ball from exiting the bore and the housing. The housing may include a stop member or plug 84 that closes one end of the bore and prevents the spring from exiting the bore. Here, stop member 84 is formed as a cylinder that is press-fit into bore 78.

One skilled in the art will appreciate that the locking member and biasing member can have various other configurations besides a ball and spring and still be within the scope of the invention. The locking member, for example, can be a pin, button, roller, cylinder, or the like. Further, the biasing member can be a coiled spring or any one of various biasing devices known to those skilled in the art.

Looking now to FIGS. 1 and 2, the function of the retention mechanism is shown. When the impression coping 10 is connected to the dental implant 12, the indexing portion 40 engages the bore 18. Here, the retention mechanism 38 functions to hold the impression coping to the implant. Specifically, the biasing member 64 biases the locking member 62 against an internal surface or wall in bore 18 of the implant. This engagement between the locking member and wall is sufficient to hold and retain the impression coping to the implant.

Preferably, the locking member 62 is formed from hard material, such as ceramic, ruby, or silicone nitride. As one advantage, a ceramic ball will not leave a residue or deposit on the internal surface or wall of the implant where the implant and ball contact.

Preferably, the biasing member 64 is formed from a biocompatible, corrosive resistant material, such as titanium. Other materials include stainless steel (such as SS 17-4) coated with an amorphous diamond coating. For example, a titanium spring is biocompatible and will not corrode.

One advantage of the present invention is that the connection between the impression coping and the implant is consistent and reliable. This connection is not based on a frictional taper fit or a snap-fit but on an active or moveable locking member and biasing member. Further, the retention mechanism will not damage the internal cavity of the implant or leave micro-fragments or residuals from the locking member.

Figure 4:
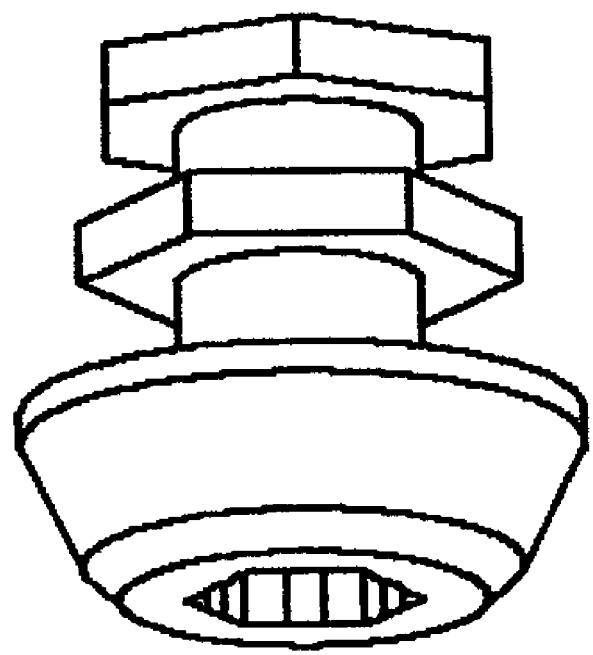
FIG. 4 illustrates an exploded view of an alternate embodiment of the impression coping of the present invention.
Figure 4:
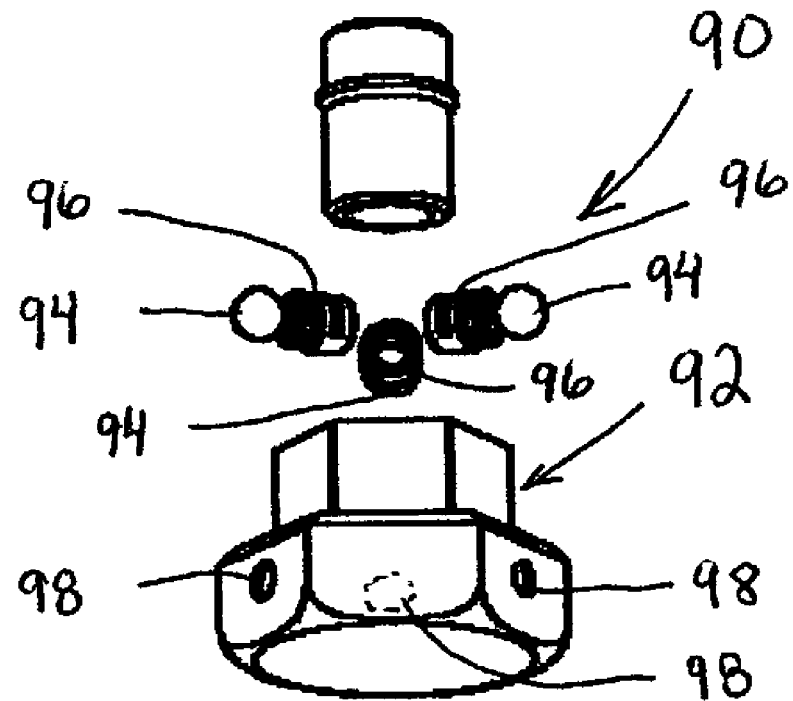

It will be appreciated that the present invention could incorporate a housing and retention mechanism with other configurations not departing from the scope of the invention. FIG. 4 shows one such example. Here, the retention mechanism 90 includes a housing 92 and three locking members 94 and three biasing members 96 located in the housing. The housing 92 and retention mechanism 90 generally have a configuration similar to the housing 60 and retention mechanism 38 described in FIGS. 1–3. As one important difference, the housing 92 includes three separate axial bores 98 (one being shown in phantom). Each axial bore houses a single locking member 94 and a biasing member 96. These members are illustrated as a ball and spring and slideably move in the bore as described in FIGS. 1–3.

Other embodiments are within the scope of the invention too. Various combinations of multiple balls and springs can be used. Two balls, for example, could be employed in a single bore that extended entirely across the housing; one ball could be positioned at the first end of the spring and a second ball at the other end. Further, as illustrated in FIG. 4, multiple bores could be used to house multiple balls and springs.

As one advantage of the present invention, the impression coping is well suited for multi-teeth restorations, especially when some of the implants are angled with respect to one another. In this situation, when the implants are not all vertically oriented, the copings are less prone to jam or wedge when the impression tray is lifted and removed from the mouth of the patient. Specifically, the ball or balls of the retention mechanism are able to slideably move into the housing and out of engagement with the surface of the implant. This movement helps to prevent the copings from becoming wedged or jammed while engaged with the implant.

As another important advantage of the present invention, connection between the coping and implant does not require a separate retaining screw. Rather, the connection occurs with active or moveable biasing and locking members. Since a retaining screw is not needed, several steps can be eliminated while performing an open-tray impression technique. These steps include: threading the screw into the implant; opening or drilling holes in the impression tray; and unthreading the screw prior to removing the coping from the implantation site. The elimination of these steps saves valuable time during the dental surgery and reduces costs.

As understood by those skilled in the art, the precise configuration and dimensions of the various components of the impression coping may vary depending upon, for example, the kind and size of the implant, the location of the osteotomy, or the number and formation of impressions to be taken. Further, it will be appreciated that the impression coping can be configured and used as either a pick-up type coping or as a transfer type coping.

While preferred embodiments of this invention have been shown and described, modifications thereof can be made by one skilled in the art without departing from the spirit or teaching of this invention. The embodiments described herein are exemplary only and are not limiting. Many variations and modifications of the system, apparatus, and methods are possible and are within the scope of the inventions claimed below. Accordingly, the scope of protection is not limited to the embodiments described herein, but is only limited by the claims that follow, the scope of which shall include all equivalents of the subject matter of the claims.

What is claimed is:

1. An impression coping for recording the position and orientation of a dental implant installed in a jawbone of a patient, the impression coping comprising:
   a body having proximal and distal portions, the proximal portion having an attachment portion adapted to be embedded in an impression material, the distal portion having a retention mechanism adapted to releasably engage a coronal end of the dental implant, wherein the retention mechanism includes a locking member and a biasing member slideably moveable in a bore to bias the locking member against the coronal end of the dental implant, wherein the biasing member is a spring adapted to bias the locking member against an internal cavity of the dental implant, and wherein the locking member is formed of a ceramic and the spring is formed of a corrosive resistant metal.

2. The impression coping of claim 1 wherein the locking member is formed of one of ruby or silicone nitride, and the spring is formed of one of titanium or steel.

3. An impression coping for recording the position and orientation of a dental implant installed in a jawbone of a patient, the impression coping comprising:
   a body having proximal and distal portions, the proximal portion having an attachment portion adapted to be embedded in an impression material, the distal portion having a retention mechanism adapted to engage a coronal end of the dental implant, wherein the retention mechanism includes a locking member and a biasing member slideably moveable in a bore to bias the locking member against the coronal end of the dental implant, wherein the biasing member is a spring adapted to bias the locking member against an internal cavity of the dental implant and wherein the locking member is formed of a ceramic and the spring is formed of a corrosive resistant metal.

4. The impression coping of claim 3 wherein the locking member is formed of one of ruby or silicone nitride, and the spring is formed of one of titanium or steel.

5. The impression coping of claim 3 wherein the attachment portion includes two separate and spaced polygonal attachment members.

6. The impression coping of claim 5 wherein the attachment members are one of a triangle, square, hexagon, octagon, or star.

7. An impression coping, comprising:
   a body having a proximal portion adapted to be embedded in impression material and a distal portion with a retention mechanism adapted to engage a coronal end of a dental implant, wherein the retention mechanism includes a housing, a locking member, and a biasing member, wherein the biasing member biases the locking member to slideably move in the housing, wherein the biasing member is adapted to bias the locking member against a surface at the coronal end of the dental implant, wherein the housing includes a bore, wherein the locking and biasing members slideably move in the bore, wherein the locking member is formed of a ceramic, and the biasing member is formed of a corrosive resistant metal, and wherein the biasing member is one of ruby or silicone nitride, and the biasing member is one of titanium or steel.

* * * * *